US012569412B2

(12) United States Patent
Kaminosono et al.

(10) Patent No.: US 12,569,412 B2
(45) Date of Patent: Mar. 10, 2026

(54) BASE PASTE AND DENTAL ADDITIVE SILICONE IMPRESSION MATERIAL

(71) Applicant: GC Corporation, Shizuoka (JP)

(72) Inventors: Yoshiya Kaminosono, Tokyo (JP); Chiaki Oizumi, Tokyo (JP); Teppei Ito, Tokyo (JP); Yuki Shibuya, Tokyo (JP)

(73) Assignee: GC Corporation, Shizuoka (JP)

( * ) Notice: Subject to any disclaimer, the term of this patent is extended or adjusted under 35 U.S.C. 154(b) by 840 days.

(21) Appl. No.: 17/755,835

(22) PCT Filed: Jul. 29, 2020

(86) PCT No.: PCT/JP2020/029043
§ 371 (c)(1),
(2) Date: May 10, 2022

(87) PCT Pub. No.: WO2021/100251
PCT Pub. Date: May 27, 2021

(65) Prior Publication Data
US 2022/0401314 A1     Dec. 22, 2022

(30) Foreign Application Priority Data

Nov. 19, 2019     (JP) ................................ 2019-208568

(51) Int. Cl.
*A61K 6/90*          (2020.01)
*A61K 6/60*          (2020.01)
(52) U.S. Cl.
CPC . *A61K 6/90* (2020.01); *A61K 6/60* (2020.01)

(58) Field of Classification Search
None
See application file for complete search history.

(56) References Cited

U.S. PATENT DOCUMENTS

| | | | |
|---|---|---|---|
| 4,877,854 A | 10/1989 | Hattori et al. |
| 5,086,148 A | 2/1992 | Jochum et al. |
| 2003/0125411 A1 | 7/2003 | Kamohara |
| 2004/0152858 A1 | 8/2004 | Kamohara et al. |
| 2010/0069525 A1 | 3/2010 | Kamohara et al. |
| 2012/0083549 A1 | 4/2012 | Kamohara et al. |

FOREIGN PATENT DOCUMENTS

| | | |
|---|---|---|
| JP | H04-293955 | 10/1992 |
| JP | H06-037558 | 5/1994 |
| JP | 2003-081732 | 3/2003 |
| JP | 2004-182823 | 7/2004 |
| JP | 2009-203196 | 9/2009 |
| JP | 2010-070643 | 4/2010 |
| JP | 2012-076999 | 4/2012 |

OTHER PUBLICATIONS

International Search Report for PCT/JP2020/029043 mailed on Sep. 24, 2020.

*Primary Examiner* — Robert T Butcher
(74) *Attorney, Agent, or Firm* — IPUSA, PLLC

(57)          ABSTRACT

One aspect of the present invention is a base paste for a dental additive silicone impression material, the base paste includes a polyether having a peak molecular weight of 1,000 or less, wherein at least one terminal end of the polyether is sealed with an alkenyl group.

5 Claims, No Drawings

BASE PASTE AND DENTAL ADDITIVE SILICONE IMPRESSION MATERIAL

TECHNICAL FIELD

The present invention relates to a base paste, a dental additive silicone impression material, a method of manufacturing the base paste, and a method of manufacturing the dental additive silicone impression material.

BACKGROUND ART

In the dental field, additive silicone impression materials are widely used to obtain dental impressions.

The additive silicone impression material includes an organopolysiloxane having an alkenyl group, an organohydrogenpolysiloxane, and a hydrosilylation catalyst (for example, Patent Document 1).

RELATED ART DOCUMENTS

Patent Documents

[Patent Document 1] Japanese Patent Application Laid-Open No. 2012-76999

SUMMARY OF INVENTION

Problem to be Solved by the Invention

In this case, the working time of the additive silicone impression material may be increased in consideration of clinical comfort.

For example, adding divinyltetramethyldisiloxane to the base paste increases the working time of the additive silicone impression material.

However, there has been a problem in that the delayed curing of the additive silicone impression material occurs.

One aspect of the present invention is to provide a base paste capable of suppressing the delayed curing of the dental additive silicone impression material even if the working time of the dental additive silicone impression material is increased.

Means for Solving Problem

One aspect of the present invention is a base paste for a dental additive silicone impression material, the base paste includes a polyether having a peak molecular weight of 1,000 or less, wherein at least one terminal end of the polyether is sealed with an alkenyl group.

Another aspect of the present invention is a method of manufacturing a base paste for a dental additive silicone impression material, the method includes producing a base paste using a polyether having at least one terminal end of the polyether sealed with an alkenyl group and having a peak molecular weight of 1,000 or less.

Effects of the Invention

According to an aspect of the present invention, the present invention is to provide a base paste capable of suppressing the delayed curing of the dental additive silicone impression material even if the working time of the dental additive silicone impression material is increased.

MODE FOR CARRYING OUT THE INVENTION

Next, embodiments for carrying out the present invention will be described.

[Dental Additive Silicone Impression Materials]

The dental additive silicone impression material of the present embodiment includes a base paste and a catalyst paste.

That is, the dental additive silicone impression material of the present embodiment is a two-paste type having both a base paste including an organohydrogenpolysiloxane and a catalyst paste including a hydrosilylation catalyst.

The base paste typically includes both an organopolysiloxane having an alkenyl group and an organohydrogenpolysiloxane, and these components are mixed to prepare the base paste.

The catalyst paste typically includes both an organopolysiloxane having an alkenyl group and a hydrosilylation catalyst, and these components are mixed to prepare the catalyst paste.

In obtaining an impression, for example, a kneaded mix of the base paste and the catalyst paste is built up in a tray or mouth and left to cure in a mouth.

[Base Paste]

The base paste includes a polyether having a peak molecular weight of 1000 or less and at least one terminal end of the polyether is sealed with an alkenyl group (hereinafter, referred to as "polyether A"). Therefore, the delayed curing of the dental additive silicone impression material is suppressed even if the working time of the dental additive silicone impression material is increased.

[Polyether A]

Preferably, the peak molecular weight of polyether A is 1,000 or less and preferably 600 or less. If the peak molecular weight of polyether A exceeds 1,000, the delayed curing of the dental additive silicone impression material occurs when the working time of the dental additive silicone impression material is increased.

The peak molecular weight of polyether A is measured, for example, by liquid chromatography.

A constituent unit of the polyether A is preferably an oxyalkylene group.

Examples of the oxyalkylene groups include an oxyethylene group, an oxypropylene group, an oxytetramethylene group, and the like. Two or more kinds of oxyalkylene groups may be used in combination.

Examples of the alkenyl groups that seal the terminal end of the polyether A include an allyl group, a vinyl group, and the like. Two or more kinds of alkenyl groups may be used in combination.

The polyether A may be sealed at both terminal ends with an alkenyl group, but preferably one terminal end is sealed with an alkenyl group and the other terminal end is sealed with a hydrogen atom or an alkyl group. This further suppresses the delayed curing of the dental additive silicone impression material even if the working time of the dental additive silicone impression material is increased.

Examples of the alkyl groups that seal the terminal end of the polyether A include a methyl group, an ethyl group, a propyl group, a butyl group, an isopropyl group, and the like.

A mass ratio of the polyether A to the total amount of the organopolysiloxane having an alkenyl group and the organohydrogenpolysiloxane in the dental additive silicone impression material is preferably 0.01 to 10% by mass, and further preferably 0.1 to 5% by mass. If the mass ratio of the polyether A to the total amount of the organopolysiloxane having the alkenyl group and the organohydrogenpolysiloxane in the dental additive silicone impression material is 0.01% by mass or more, the delayed curing of the dental additive silicone impression material is further suppressed even if the working time of the dental additive silicone impression material is increased. If the mass ratio of the polyether A to the total amount of the organopolysiloxane having the alkenyl group and the organohydrogenpolysiloxane in the dental additive silicone impression material is 10% by mass or less, the working time of the dental additive silicone impression material can be further increased.

It should be noted that two or more kinds of polyether A may be used in combination.

[Organopolysiloxane Having Alkenyl Group]

The organopolysiloxane having an alkenyl group is not particularly limited as long as the organopolysiloxane having an alkenyl group can hydrosilylate with the organohydrogenpolysiloxane.

The organopolysiloxane having an alkenyl group is preferably represented by the following average composition formula:

$$R^1_a SiO_{(4-a)/2}$$

(wherein $R^1$ is a substituted or unsubstituted monovalent hydrocarbon group having 1 to 10 carbons and preferably 1 to 8 carbons; a is 1.95 to 2.05 and preferably 2.00 to 2.02; among the number of a in the $R^1$, 0.0001 to 20 mol %, preferably 0.001 to 10 mol %, and even more preferably 0.01 to 5 mol % of an alkenyl group having 2 to 8 carbons and preferably 2 to 6 carbons).

Examples of the monovalent hydrocarbon groups in $R^1$ include alkyl groups such as a methyl group, ethyl group, propyl group, isopropyl group, butyl group, isobutyl group, tert-butyl group, pentyl group, neopentyl group, hexyl group, cyclohexyl group, octyl group, nonyl group, decyl group, and the like; aryl groups such a phenyl group, tolyl group, xylyl group, naphthyl group and the like; aralkyl groups such a benzyl group, phenylethyl group, phenylpropyl group, and the like; alkenyl groups such as a vinyl group, allyl group, propenyl group, isopropenyl group, butenyl group, hexenyl group, cyclohexenyl group, octenyl group, and the like.

Examples of substituents in $R^1$ include halogen atoms such as fluorine atom, bromine atom, chlorine atom, and the like, and cyano group, and the like.

Examples of alkyl groups substituted by substituent groups include a chloromethyl group, chloropropyl group, bromoethyl group, trifluoropropyl group, cyanoethyl group, and the like.

The alkenyl group may be bonded to a silicon atom at the terminal end or may be bonded to a silicon atom at other than the terminal end, and preferably is bonded to a silicon atom at the both terminal ends.

$R^1$ other than an alkenyl group is preferably a methyl group or a phenyl group.

The organopolysiloxane having alkenyl groups preferably have two or more alkenyl groups.

The organopolysiloxane having alkenyl groups includes an M unit and a D unit, and may further include a T unit.

The organopolysiloxane having alkenyl groups can also be either homopolymers or copolymers.

Examples of the organopolysiloxane having alkenyl groups include dimethyl polysiloxane having both terminal ends sealed with a dimethylvinyl siloxy group; dimethyl polysiloxane having both terminal ends sealed with a methyldivinylsiloxy group; dimethylsiloxane (80 mol %)-methylphenylsiloxane (20 mol %) copolymer having both terminal ends sealed with a dimethylvinyl siloxy group; dimethylsiloxane (80 mol %)-diphenylsiloxane (20 mol %) copolymer having both terminal ends sealed with a dimethylvinyl siloxy group; dimethylsiloxane (90 mol %)-diphenylsiloxane (10 mol %) copolymer having both terminal ends sealed with a dimethylvinyl siloxy group; and dimethylsiloxane-methylvinylsiloxane copolymer having both terminal ends sealed with a trimethylsiloxy group; and the like.

An organopolysiloxane having two or more kinds of alkenyl groups may also be used in combination.

[Organohydrogenpolysiloxane]

The organohydrogenpolysiloxane is not particularly limited as long as the organohydrogenpolysiloxane can hydrosilylate with the organopolysiloxane having an alkenyl group.

The organohydrogenpolysiloxane is preferably represented as the following average composition formula:

$$R^2_b H_c SiO_{(4-b-c)/2}$$

(wherein $R^2$ is a substituted or unsubstituted monovalent hydrocarbon group of 1 to 10 carbons, b is 0.7 to 2.1, c is 0.001 to 1.0, and b+c is 0.8 to 3.0).

The organohydrogenpolysiloxane preferably has three or more hydrosilyl groups.

Here, $R^2$ is similar to $R^1$ in the organopolysiloxane having an alkenyl group, but preferably without an aliphatic unsaturated bond.

Examples of organohydrogenpolysiloxanes include 1,1,3,3-tetramethyldisiloxane, 1,3,5,7-tetramethyl cyclotetrasiloxane, methylhydrogencyclopolysiloxane, methylhydrogensiloxane-dimethylsiloxane cyclic copolymer, tris (dimethylhydrogensiloxy) methylsilane, tris (dimethylhydrogensiloxy) phenylsilane, methylhydrogenpolysiloxane in which both terminal ends are sealed with trimethylsiloxy groups, dimethylsiloxane-methylhydrogensiloxane copolymer in which both terminal ends are sealed with trimethylsiloxy groups, dimethylpolysiloxane in which both terminal ends are sealed with dimethylhydrogensiloxy groups, dimethylsiloxane-methylhydrogensiloxane copolymer in which both terminal ends are sealed with dimethylhydrogensiloxy groups, methyl hydrogenpolysiloxane in which both terminal ends are sealed with dimethylhydrogensiloxy group, methyl hydrogensiloxane-diphenylsiloxane copolymer in which both terminal ends are sealed with trimethylsiloxy groups, methyl hydrogensiloxane-diphenylsiloxane-dimethylsiloxane copolymer in which both terminal ends are sealed with trimethylsiloxy groups, copolymer consisting of $(CH_3)_2 HSiO_{1/2}$ units and $SiO_{4/2}$ units, and copolymer having $(CH_3)_2 HSiO_{1/2}$ units, $SiO_{4/2}$ units, and $(C_6H_5)SiO_{3/2}$ units, and the like.

The organohydrogenpolysiloxane may be linear, cyclic, or branched.

The number of silicon atoms present in the organohydrogenpolysiloxane is preferably 2 to 1,000, more preferably 3 to 300, and even more preferably 4 to 100.

Two or more kinds of organohydrogenpolysiloxanes may be used in combination.

A molar ratio of the hydrosilyl group of the organohydrogenpolysiloxane to the alkenyl group of the organopolysiloxane having an alkenyl group in the dental additive silicone impression material is 0.1 to 4.0.

[Hydrosilylation Catalyst]

The hydrosilylation catalyst is not particularly limited as long as the hydrosilylation catalyst can promote the hydrosilylation reaction of the organopolysiloxane having an alkenyl group and the organohydrogenpolysiloxane. Examples of hydrosilylation catalysts include platinum-group metal catalysts such as black platinum, secondary platinum chloride, platinum chloride acid, a reaction product of platinum chloride acid and a monohydric alcohol, a complex of platinum chloride acid and olefins, a platinum-based catalyst such as platinum bis-acetoacetate, a palladium-based catalyst, and a rhodium-based catalyst.

Two or more kinds of hydrosilylation catalysts may be used in combination.

[Other Components]

The base paste of the present embodiment may further contain a polyether having a peak molecular weight greater than 1,000 and 10,000 or less (hereinafter referred to as polyether B), a filler, a nonionic surfactant, or the like, wherein at least one terminal end of the polyether B is sealed with an alkenyl group. The catalyst paste may also include a filler or the like.

The polyether B is the same as the polyether A except that the peak molecular weight is different.

Examples of the filler materials include aerosol silica particles, wet-type silica particles, crystalline silica particles, carbon black, Bengala particles, cerium oxide particles, titanium oxide particles, calcium carbonate particles, aluminum hydroxide particles, titanate particles, and the like.

Two or more kinds of fillers may be used in combination.

Examples of nonionic surfactants include silicone-based surfactants, hydrocarbon-based surfactants (for example, polyoxyethylene alkyl ethers), fluorocarbon surfactants, and the like. Among them, silicone-based surfactants and hydrocarbon-based surfactants are preferably used.

Examples of commercially available silicone-based surfactants include KF-351A, KF945, KF640, KF642, KF643, KF644 (manufactured by Shin-Etsu Chemical Co., Ltd.) and the like.

Examples of commercially available hydrocarbon-based surfactants include Naroacty CL40, CL50, CL70, CL90, Sannonic SS30, SS50, SS70, SS90 (manufactured by Sanyo Chemical Co., Ltd.) and the like.

Two or more kinds of nonionic surfactants may be used in combination.

EXAMPLES

Hereinafter, examples of the present invention will be described, but the present invention is not limited to examples.

Examples 1 to 7, Comparative Examples 1 to 4

As indicated in Table 1, the components [% by mass] such as a polyether, silica particles, vinyl polysiloxane, organo-hydrogenpolysiloxane, a nonionic surfactant, a hydrosilylation catalyst, and divinyltetramethyldisiloxane were mixed to prepare an additive silicone impression material having a catalyst paste (hereinafter, referred to as paste A) and a base paste (hereinafter, referred to as paste B).

The details of each component in Table 1 are as follows.

Polyether A1: Uniox PKA-5003 (polyethylene glycol allyl ether with an average molecular weight of 450) (manufactured by NOF Corporation)

Polyether A2: Uniox PKA-5007 (methoxypolyethylene glycol allyl ether with an average molecular weight of 400) (manufactured by NOF Corporation)

Polyether A3: Uniox AA-800 (polyethylene glycol diallyl ether with an average molecular weight of 800) (manufactured by NOF Corporation)

Polyether B1: UNISAFE PKA-5015 (butoxypolyethylene glycol polypropylene glycol allyl ether with an average molecular weight of 1,600, EC/PO molar ratio: 75/25) (manufactured by NOF Corporation)

Polyether B2: UNISAFE PKA-5016 (Butoxypolyethylene glycol polypropylene glycol allyl ether with an average molecular weight of 1,600, EO/PO molar ratio: 50/50) (manufactured by NOF Corporation)

Silica particles: CRYSTALITE VX-S (manufactured by Tatsumori)

Vinyl polysiloxane: dimethyl polysiloxane in which both terminal ends are sealed with vinyl dimethyl siloxy groups and the viscosity is 10 Pas at 25° C.

Organohydrogenpolysiloxane: Linear methylhydrogen-polysiloxane in which a content of methylhydrogensiloxy group is 40% by mol Nonionic surfactant 1: Naroacty CL-40 (polyoxyethylene alkyl ether) (manufactured by Sanyo Chemical Industries, Ltd.)

Nonionic surfactant 2: Sannonic SS-50 (polyoxyethylene alkyl ether) (manufactured by Sanyo Chemical Industries, Ltd.)

Nonionic surfactant 3: KF-643 (silicone-based surfactant) (manufactured by Shin-Etsu Chemical Co., Ltd.)

Nonionic surfactant 4: KF-644 (silicone-based surfactant) (manufactured by Shin-Etsu Chemical Co., Ltd.)

Hydrosilylation catalyst: 0.4% by mass of silicone oil solution of platinum 1,3-divinyl-1,1,3,3-tetramethyldisiloxane complex

[Peak Molecular Weight of Polyether]

The peak molecular weight of polyether was measured under the following conditions using the high-performance liquid chromatograph Shodex GPC-104 (manufactured by Showa Denko K.K.) and column LF-604 (manufactured by Showa Denko K.K.).

Solvent: THF

Column temperature: 40° C.

Flow rate: 0.5 mL/min

Pump pressure: 2.3 MPa

Detection: UV

Polyethylene glycol 200, 300, 400, 600, 1000, 1540, and 2000 (manufactured by FUJIFILM Wako Pure Chemical Corporation) was used as the standard sample.

The measurement results of the peak molecular weight of polyether are shown below.

Polyether A1: 520
Polyether A2: 480
Polyether A3: 870
Polyether B1: 1,800
Polyether B2: 2,000

Next, the working time, curing time, and tear strength of the cured material of the additive silicone impression material were evaluated.

[Working Time]

The paste A and the paste B were kneaded in a mass ratio of 1:1 in a constant temperature room at 23° C. The kneaded mixture was then touched with a spatula to determine the time until the kneading could not be performed. The time was determined as the working time.

[Curing Time]

In the constant temperature room at 23° C., the paste A and the paste B were kneaded in a mass ratio of 1:1. The kneaded mixture was inputted into a metal ring with an inner diameter of 24 mm and a height of 8 mm. A 150 g of Vickers needle with a diameter of 3 mm was then dropped into the kneaded mixture. The time until the penetration of the Vickers needle from the surface of the kneaded mixture to be 1 mm or less was measured and determined as the curing time.

[Tear Strength of Cured Material]

In accordance with JIS T 6527, the paste A and the paste B were kneaded at a mass ratio of 1:1, the tear strength test of the cured material which was cured at the curing time described above was then performed, and the tear strength of the cured material was measured.

Table 1 indicates the evaluation results of the working time, curing time, and tear strength of the cured material of the additive silicone impression material.

TABLE 1

| | Examples | | | | | | | | | | |
|---|---|---|---|---|---|---|---|---|---|---|---|
| | 1 | | 2 | | 3 | | 4 | | 5 | | 6 |
| Paste | A | B | A | B | A | B | A | B | A | B | A |
| Polyether A1 | | 1 | | | | | | | | | |
| Polyether A2 | | | | 1 | | | | | | 1 | |
| Polyether A3 | | | | | | 1 | | 2 | | | |
| Polyether B1 | | | | | | | | | | | |
| Polyether B2 | | | | | | | | | | | |
| Silica particles | 40 | 40 | 50 | 50 | 60 | 60 | 70 | 70 | 70 | 70 | 50 |
| Vinyl polysiloxane | 59 | 49 | 49 | 39 | 39 | 29 | 29 | 22 | 29 | 23 | 49 |
| Organohydrogenpolysiloxane | | 5 | | 5 | | 5 | | 5 | | 5 | |
| Nonionic surfactant 1 | | 5 | | | | | | | | | |
| Nonionic surfactant 2 | | | | 5 | | | | | | | |
| Nonionic surfactant 3 | | | | | | 5 | | | | | |
| Nonionic surfactant 4 | | | | | | | | 1 | | 1 | |
| Hydrosilylation catalyst | 1 | | 1 | | 1 | | 1 | | 1 | | 1 |
| Divinyl tetramethyldisiloxane | | | | | | | | | | | |
| Total | 100 | 100 | 100 | 100 | 100 | 100 | 100 | 100 | 100 | 100 | 100 |
| Mass ratio of polyether A to the total amount of organopolysiloxane and organohydrogenpolysiloxane [%] | 0.88 | | 1.08 | | 1.37 | | 3.57 | | 1.75 | | 1.14 |
| Working time | 3'15" | | 3'00" | | 3'00" | | 3'00" | | 3'00" | | 3'00" |
| Curing time | 5'15" | | 5'00" | | 4'45" | | 5'30" | | 5'30" | | 5'15" |
| Tear strength [N/mm] | 3.5 | | 3.7 | | 4.0 | | 3.5 | | 4.2 | | 3.6 |

| | Examples | | | Comparative Examples | | | | | | | |
|---|---|---|---|---|---|---|---|---|---|---|---|
| | 6 | 7 | | 1 | | 2 | | 3 | | 4 | |
| Paste | B | A | B | A | B | A | B | A | B | A | B |
| Polyether A1 | | | | | | | | | | | |
| Polyether A2 | 1 | | 1 | | | | | | | | |
| Polyether A3 | | | | | | | | | | | |
| Polyether B1 | 5 | | | | | | 5 | | | | |
| Polyether B2 | | | 5 | | | | | | 5 | | |
| Silica particles | 50 | 50 | 50 | 40 | 40 | 40 | 40 | 40 | 40 | 40 | 40 |
| Vinyl polysiloxane | 34 | 49 | 34 | 59 | 50 | 59 | 45 | 59 | 45 | 59 | 49.9 |
| Organohydrogenpolysiloxane | 5 | | 5 | | 5 | | 5 | | 5 | | 5 |
| Nonionic surfactant 1 | | | | | 5 | | 5 | | 5 | | 5 |
| Nonionic surfactant 2 | 5 | | 5 | | | | | | | | |
| Nonionic surfactant 3 | | | | | | | | | | | |
| Nonionic surfactant 4 | | | | | | | | | | | |
| Hydrosilylation catalyst | | 1 | | 1 | | 1 | | 1 | | 1 | |
| Divinyl tetramethyldisiloxane | | | | | | | | | | | 0.1 |
| Total | 100 | 100 | 100 | 100 | 100 | 100 | 100 | 100 | 100 | 100 | 100 |
| Mass ratio of polyether A to the total amount of organopolysiloxane and organohydrogenpolysiloxane [%] | 1.14 | 1.14 | | — | | — | | — | | — | |
| Working time | 3'00" | 3'00" | | 1'00" | | 1'00" | | 1'00" | | 3'00" | |
| Curing time | 5'15" | 5'15" | | 2'00" | | 2'15" | | 2'15" | | 7'00" | |
| Tear strength [N/mm] | 3.6 | 3.6 | | 3.5 | | 3.4 | | 3.4 | | 3.5 | |

From Table 1, it can be seen that the additive silicone impression material of Examples 1 to 7 suppresses the delayed curing even if the working time is increased.

On the other hand, the additive silicone impression material in Comparative Example 1 contains the paste B not having the polyether A, and thus the working time is short.

The additive silicone impression materials in Comparative Examples 2 and 3 do not contain the polyether A in the paste B, but contains the polyether B, and thus the working time is short.

The additive silicone impression material of Comparative Example 4 does not contain the polyether A in the paste B, but contains divinyltetramethyldisiloxane, resulting in the delayed curing.

This application is based upon and claims priority to Japanese Patent Application No. 2019-208568, filed on Nov. 19, 2019, the entire contents of which are incorporated herein by reference.

The invention claimed is:

1. A base paste for a dental additive silicone impression material, the base paste comprising:
   a filler;
   an organopolysiloxane having an alkenyl group;
   an organohydrogenpolysiloxane; and
   at least one of a polyethylene glycol allyl ether having a peak molecular weight of 1,000 or less or a derivative of the polyethylene glycol allyl ether,
   wherein one terminal end of the polyethylene glycol allyl ether is sealed with an alkenyl group and the other terminal end of the polyethylene glycol allyl ether is sealed with a hydrogen atom or an alkyl group, and the organohydrogenpolysiloxane is at least one selected from a group consisting of 1,1,3,3-tetramethyldisiloxane and dimethylpolysiloxane having both terminal ends sealed with dimethylhydrogensiloxy groups.

2. The base paste according to claim 1, wherein the at least one of the polyethylene glycol allyl ether having the peak molecular weight of 1,000 or less or the derivative of the polyethylene glycol allyl ether is the polyethylene glycol allyl ether, a methoxypolyethylene glycol allyl ether, or both.

3. A dental additive silicone impression material comprising:

the base paste of claim 1; and a catalyst paste.

4. A method of manufacturing a base paste of claim 1, the method comprising:

producing a base paste using at least one of a polyethylene glycol allyl ether having a peak molecular weight of 1,000 or less or a derivative of the polyethylene glycol allyl ether, wherein one terminal end of the polyethylene glycol allyl ether is sealed with an alkenyl group and the other terminal end of the polyethylene glycol allyl ether is sealed with a hydrogen atom or an alkyl group.

5. A method of manufacturing a dental additive silicone impression material, the method comprising:

producing a base paste by the method of producing the base paste of claim 4; and producing a catalyst paste.

* * * * *